United States Patent [19]

Retzer et al.

[11] 4,003,662
[45] Jan. 18, 1977

[54] PORTABLE PHOTOMETER

[75] Inventors: Erich Retzer, Maisach; Otto Holzinger, Munich; Wilhelm Pross, Munich, all of Germany

[73] Assignee: Compur-Electronic Gesellschaft mit beschrankter Haftung, Munich, Germany

[22] Filed: May 21, 1975

[21] Appl. No.: 579,676

[30] Foreign Application Priority Data

June 4, 1974 Germany .................... 7419211

[52] U.S. Cl. .............................. 356/206; 356/40
[51] Int. Cl.² ..................................... G01N 21/24
[58] Field of Search ............... 356/40, 41, 42, 204, 356/205, 206, 208

[56] References Cited

UNITED STATES PATENTS

| | | | |
|---|---|---|---|
| 2,073,223 | 3/1937 | Rose | 356/40 |
| 2,188,097 | 1/1940 | Thompson | 356/204 |
| 2,621,557 | 12/1952 | Kavanagh | 356/40 |
| 2,749,796 | 6/1956 | Bauer | 356/204 |
| 3,008,370 | 11/1961 | Uribe | 356/40 |
| 3,296,922 | 1/1967 | Goldberg | 356/40 |

*Primary Examiner*—John K. Corbin
*Assistant Examiner*—Richard A. Rosenberger
*Attorney, Agent, or Firm*—Stonebraker, Shepard & Stephens

[57] ABSTRACT

A photometer for measuring the light permeability of a material for testing is made portable for hand-held operation outside a laboratory for measurements such as determining the proportion of hemoglobin in human blood. It includes a battery power supply that energizes a lamp, an opening for receiving a cuvet for a measurement, and a measuring circuit having a light-sensitive element. An indicator instrument in the measuring circuit indicates zero compensation, and a manually movable wedge filter is in the path of the light beam for adjusting the light passing through the cuvet. A manually operable element effects a zero compensation of the measuring circuit before a test is made, and a viewable scale on a setting member carrying the wedge filter directly displays a test result value from adjustment of the wedge filter during measurement of the material.

10 Claims, 4 Drawing Figures

PORTABLE PHOTOMETER

BACKGROUND OF THE INVENTION

Photometers are generally known for measuring the light permeability of a reagent liquid having a predetermined proportion of a test substance mixed with the reagent liquid. The many uses for such a photometer include a determination of the proportion of hemoglobin in human blood. Prior art photometers for such purposes have been laboratory instruments that were not readily portable and were relatively slow and cumbersome to use. Moreover, the output value from prior art instruments required a calculation to adapt the valve to the particular test, and no direct reading of the output was available.

The invention involves recognition of the need for a portable photometer that can be handheld and operated for quickly and reliably making photometric measurements outside of laboratories. For example, one need for such a portable photometer is to allow doctors to measure the proportion of hemoglobin in human blood quickly and reliably at the scene of an accident or under emergency conditions. The invention aims at a conveniently portable photometer that is simple and easy to operate, accurate and reliable in making measurements, and providing a directly readable display of the test result value from any measurement.

SUMMARY OF THE INVENTION

The inventive portable photometer measures the light permeability of a material for testing and is arranged within a casing sized and shaped for handholding and manipulating. It includes a battery power supply, a lamp in circuit with the power supply, a path for a light beam from the lamp, and a manually operable switch for energizing the lamp. It also includes a conductor plate and an electrically measuring circuit having elements connectable to the conductor plate, with the measuring circuit including at least one light-sensitive element. A wedge filter is movably arranged in the path of the light beam, and a manually movable setting member positions the wedge filter. The measuring circuit also includes an indicator instrument having a pointer cooperating with an index mark for indicating zero compensation of the measuring circuit, which is effected by a manually operable element in the measuring circuit before a test measurement. The casing has an opening for receiving a cuvet containing the material to be tested, so the cuvet is positioned in the path of the light beam, and a viewable scale movable by the setting member with movement of the wedge filter displays a directly readable test result value from adjustment of the wedge filter during a measurement of the material.

The scale and the wedge filter are preferably arranged on the setting member, and viewing windows for the instrument pointer and the scale are preferably arranged on a front face side of the casing, with the lamp switch arranged at an edge side of the casing. The setting member is preferably a disk having a knurled periphery extending outward from the opposite edge side of the casing, and the opening for receiving the cuvet is preferably also in the front face side of the casing and is normally closed by a spring-biased, hinged flap that is movable into the interior of the casing to receive the cuvet.

DETAILED DESCRIPTION OF THE INVENTION

The illustrated preferred embodiment of the inventive photometer has a relatively flat and oblong casing formed of casing halves 10 and 12 that are preferably screwed together and are preferably formed of thin-walled plastics material. The casing is sized and shaped to be held in one hand, and the instrument is relatively light so that it is readily transportable.

Figure 2:
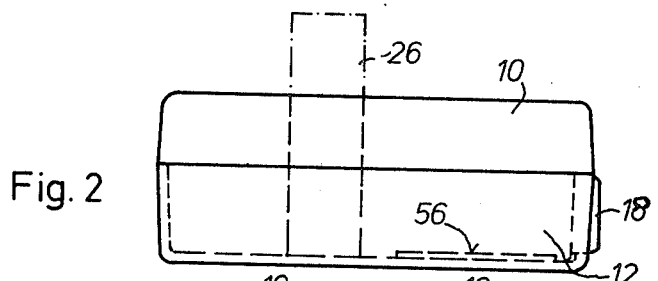
FIG. 2 is an end elevation of the photometer of FIG. 1.
Figure 3:
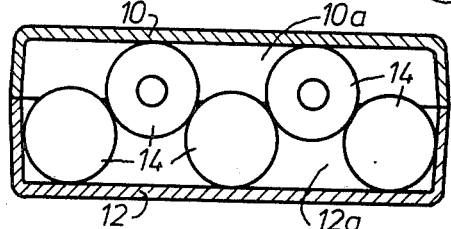
FIG. 3 is a transverse cross-sectional view of a battery power supply region of the photometer of FIG. 1.
Figure 1:
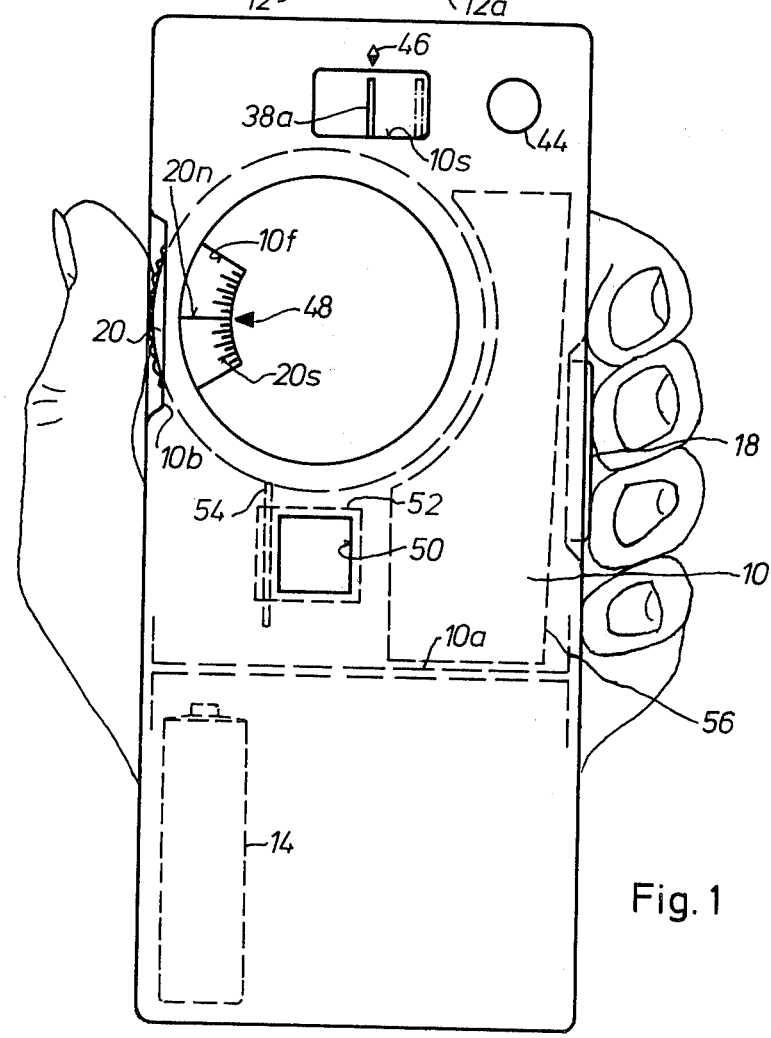
FIG. 1 is a front elevational view of a preferred embodiment of the inventive portable photometer.

A chamber formed within the casing by partition walls 10a and 12a houses a plurality of batteries 14 forming a battery power supply for the instrument. One or more batteries 14 can be used as desired, and the batteries 14 are preferably oriented axially of the casing at the lower end of the casing as illustrated. The batteries 14 provide a power supply for a lamp 16 which produces an output beam that illuminates a liquid material for a test. A finger-press switch 18 is arranged along an edge side of the casing 12 for energizing the lamp 16, and the switch 18 can be operated by the fingers of a hand holding the casing, as best shown in FIG. 1.

The remainder of the space within the casing houses the rest of the operational elements of the photometer. A setting member 20, preferably formed as a circular rotatable element with a knurled periphery, carries an arcuate wedge filter 22 and is arranged around the lamp 16 for positioning the wedge filter 22 in the path of a light beam from the lamp 16. The beam from the lamp 16 then passes through the wedge filter 22, through a focusing lens 24, and through a cuvet 26 containing a liquid material 28 formed of a reagent liquid with a test substance mixed with the reagent liquid at a predetermined ratio. The light transmitted through the cuvet 26 and the liquid 28 passes through a color filter 30 and impinges on a light-sensitive, photoelectric element 32 which produces a voltage proportional to the incident light intensity. A second photoelectric element 34 is directly exposed to light from the lamp 16 and also produces an electrical voltage.

Figure 4:
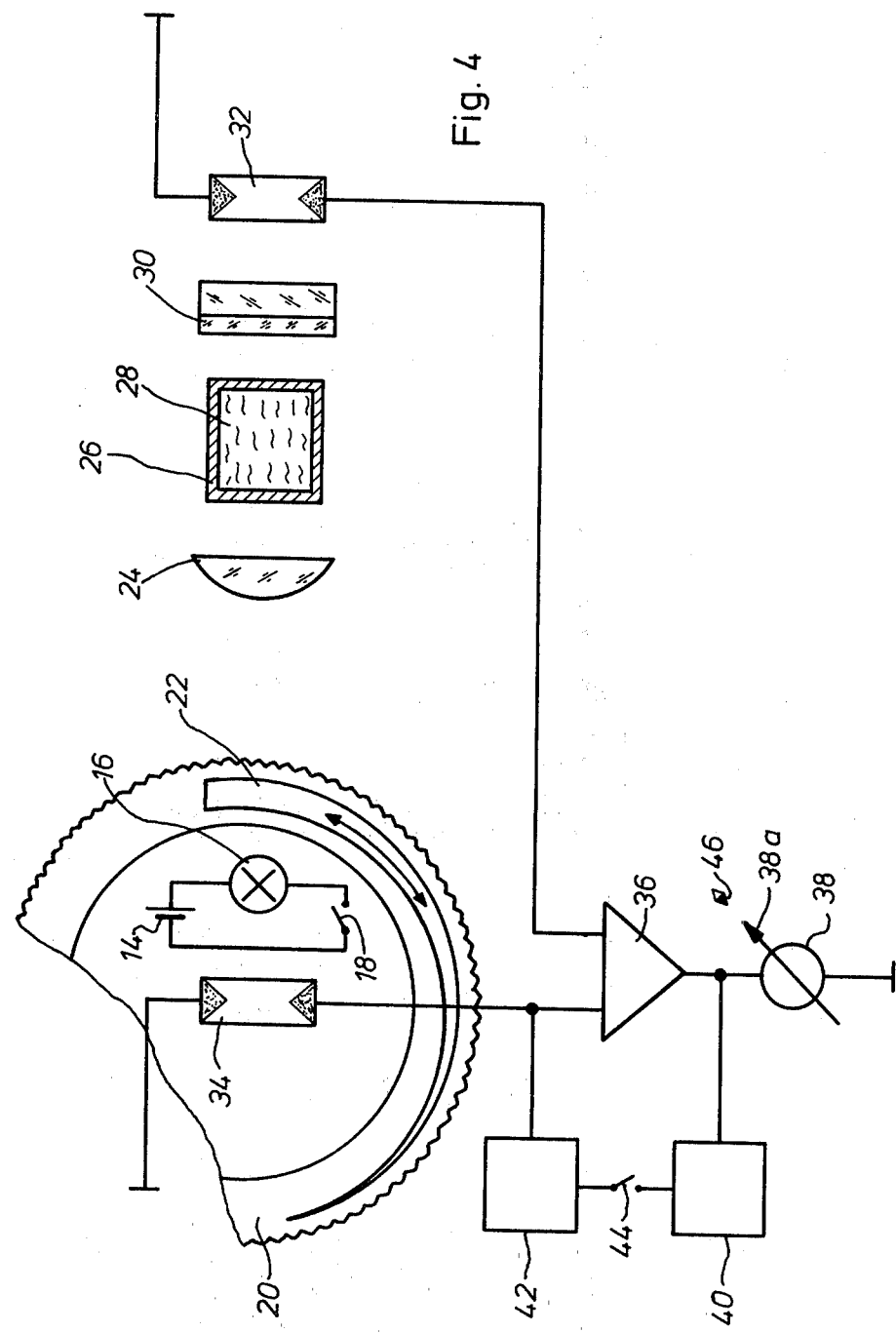
FIG. 4 is a partially schematic view of the measuring apparatus and the electrical components of the photometer of FIG. 1.

A measuring and electrical system for the inventive photometer is best shown in FIG. 4 and includes a differential amplifier 36 receiving input from photosensors 32 and 34. An indicator instrument 38 having a pointer 38a is connected to the output of amplifier 36. Power for operating the amplifier 36 and other elements of the measuring circuitry is derived from the battery supply 14 in a generally known way so that circuitry for the power supply has been omitted from FIG. 4 for simplicity's sake. The power supply is arranged for energizing the measuring circuit whenever manual press switch 18 is closed so as to operate the measuring circuit whenever the lamp 16 is energized.

The measuring circuit includes a regulating circuit 40 and a feed circuit 42 interconnected by a switch 44 and arranged in parallel with the differential amplifier 36 to eliminate possible error factors such as a varying voltage from the battery power supply 14, temperature effects, and other sources of error. The regulating circuit 40 and the feed circuit 42, when operated by the switch 44, provide a zero compensation, which is made with the cuvet 26 and its liquid 28 out of the path of the light beam from the lamp 16. The voltages produced by the photoelectric elements 32 and 34 at the two inputs to the differential amplifier 36 are balanced by the regulating circuit 40 and brought to the same value, and the feed circuit 42 insures that the resultant balancing remains stable over a predetermined time delay of a few minutes required for completing a measurement. After the inputs to the amplifier 36 are balanced, the pointer 38a of the indicator instrument 38 registers with a permanent index mark 46 on the casing part 10.

As best shown in FIG. 1, the knurled edge of the setting member 20 projects outward slightly into a recess 10b along the edge side of the casing opposite the press switch 18. This allows the thumb of the hand holding the casing to operate the setting member so that the instrument can be held and operated by one hand. A viewing window 10f near the edge of casing part 10 and next to the recess 10b permits observation of a scale 20s on the front face of the setting member 20, and the scale 20s moves relative to a fixed mark 48 on the casing. The pointer 38a of the instrument 38 is visible in another viewing window 10f also arranged in the front face surface of the casing part 10, and the pointer 38a moves relative to an index mark 46. The switch 44 for the zero compensation of the instrument is preferably a push button accessible on the front face of the casing part 10.

The front face of the casing also has a preferably square access opening 50 for receiving the cuvet 26, which preferably has a square cross section fitting the opening 50. The cuvet 26 can be inserted into the interior of the casing and into the path of the light beam from the lamp 16 for a measurement of the light permeability of the liquid 28 in the cuvet 26. A cover flap 52 is pivotally mounted on a bearing pin 54 and is biased by a spring (not shown) inside of the casing part 10 to swing closed against the interior of the opening 50 to prevent ambient light from entering the instrument. The flap 52 is swung open into the interior of the casing when the cuvet 26 is pushed into the opening 50.

A conductor plate 56 is preferably arranged within the casing to afford connections for elements of the measuring and control system. This facilitates compactness and ease of assembly but is, in itself, a generally known expedient.

In operation, the user holds the inventive photometer in his left hand and moves the setting member 20 with his left thumb until the zero mark 20n on the scale 20s registers with the index mark 48 on the casing. This positions the darkest zone of the wedge filter 22 in the path of the measuring beam from the lamp 16 and provides a base position for checking the zero compensation of the instrument. The user then presses the switch 18 with the fingers of the left hand to energize the lamp 16 and illuminate photocell 32, without the light passing through any cuvet 26; this also illuminates the photocell 34 directly. If the instrument is properly zero compensated, the pointer 38a registers with the index mark 46, and if this does not occur, the user presses the switch 44 with a finger of his right hand so that regulating circuit 40 and the feed circuit 42 automatically effect a zero compensation of the instrument and maintain the zero balance for a predetermined interval that is sufficient to complete the measurement. This moves the pointer 38a back to the index mark 46.

Then the instrument is ready for a test measurement, and the cuvet 26 previously prepared with a test material 28, is inserted, preferably with the right hand, through the opening 50 to bring the cuvet 26 and the test liquid 28 into the path of the light beam from the lamp 16 so that the intensity of the light incident on the photocell 32 is reduced by the test liquid 28. This changes the relationship of the inputs to the amplifier 36 and moves the pointer 38a of the instrument 38 away from the mark 46 to a position such as indicated in broken lines in FIG. 1. The user then moves the setting member 20 with the left thumb to adjust the wedge filter 22 to increase the light from the lamp 16 by an amount sufficient to bring the pointer 38a back to the zero position at mark 46. The adjustment of the wedge filter 22 by the setting member 20 is then related to the light permeability of the liquid 28 in the cuvet 26 and is indicated by the scale 20s. Since the instrument is preferably intended for only one type of photometric measurement, the scale 20s is graduated to display a directly readable test result value for the type of measurement being made. For example, for an instrument intended to measure the proportion of hemoglobin in human blood, the scale 20s is graduated for directly displaying the results in values relating to the hemoglobin test.

The illustrated preferred embodiment of the inventive photometer can be varied considerably within the spirit of the invention. For example, the casing can have different shapes, sizes, and forms, and switches, viewing windows, scales, and the setting member can be arranged in different ways. For example, the setting member can be made as a gear meshing with other gears for positioning a wedge filter or scale, and the setting member need not be a rotatable cylinder or disk, but can be slidable rack meshed with a pinion driving a wedge filter. The inventive instrument can be used for tests other than measuring the proportion of hemoglobin in human blood, and those skilled in the art will understand ways of applying the invention to any photometric measurement facilitated by a portable and handheld instrument. The instrument can also be made for right-handed as well as left-handed operation, and can be adapted to different sizes and shapes of cuvets. Its measuring circuitry can also be arranged in various ways.

What is claimed is:
1. A portable photometer for measuring the light permeability of a material for testing, said photometer being arranged within a casing sized and shaped for hand holding and manipulating, and said photometer comprising:
 a. a battery power supply;
 b. a lamp in circuit with said power supply;
 c. means for establishing a path for a light beam from said lamp;
 d. a manually operable switch for energizing said lamp, said switch being located and arranged for operation by fingers of a hand which holds and supports the photometer;
 e. an electrical measuring circuit;
 f. said measuring circuit including at least one light-sensitive element;
 g. a wedge filter movably arranged in said path of said light beam;

h. a manually movable setting member arranged for positioning said wedge filter, said setting member being located and arranged for manual actuation by the same hand which holds the photometer and which operates said switch for energizing said lamp;

i. said measuring circuit including an indicator instrument having a pointer cooperating with an index mark for indicating zero compensation of said measuring circuit;

j. an element arranged in said measuring circuit and manually operable for effecting said zero compensation before a test measurement;

k. said casing having an opening for receiving a cuvet containing said material so said cuvet is positioned in said path of said light beam between said lamp and said light-sensitive element and so arranged that light of said beam must pass through said cuvet in order to reach said light-sensitive element; and l. a viewable scale movable by said setting member with movement of said wedge filter for displaying a directly readable test result value from adjustment of said wedge filter during measurement of said material.

2. The photometer of claim 1 wherein said scale and said wedge filter are on said setting member.

3. The photometer of claim 1 wherein a viewing window for said pointer of said indicator instrument and a viewing window for said scale are arranged on a front face side of said casing and said switch for said lamp is arranged at an edge side of said casing.

4. The photometer of claim 3 wherein said setting member is a circular rotatable element having a knurled periphery extending outward from an opposite side edge of said casing.

5. The photometer of claim 4 wherein said scale and said wedge filter are on said setting member.

6. The photometer of claim 3 wherein said opening for receiving said cuvet is in said front face side of said casing.

7. The photometer of claim 6 including a spring-biased, hinged flap normally closing said opening and movable into the interior of said casing to receive said cuvet.

8. The photometer of claim 6 wherein said setting member is a circulator rotatable element having a knurled periphery extending outward from an opposite side edge of said casing.

9. A portable hand-held photometer designed to be held and operated entirely by one hand of a person, leaving the other hand of the person free to handle a sample to be evaluated and to place such sample in and remove it from the photometer, said photometer comprising:

a. a casing of convenient size to be held in one hand;

b. means forming an opening in said casing for receiving an at least partially transparent container holding a sample to be evaluated;

c. electric battery means within said casing;

d. a battery powered electric lamp within said casing;

e. a first light sensitive element within said casing;

f. an optical wedge mounted for calibrated movement within said casing;

g. means for directing a beam of light from said lamp along an optical path passing through said wedge and through a container within said receiving opening to said first light sensitive element;

h. a movable indicator;

i. electric circuit means operatively connected to said first light sensitive element and to said movable indicator for moving said indicator to a position dependent partly on the amount of light from said beam which falls on said first light sensitive element; and j. means manually operable by the hand which is holding said photometer for moving the position of said optical wedge to cause said movable indicator to assume a desired predetermined position.

10. A photometer as defined in claim 4, further comprising a second light sensitive element within said casing, in position to receive light directly from said lamp without passing through said wedge or said sample container, and an electronic comparator amplifier, said electric circuit means including means for supplying one input to said comparator amplifier from said first light sensitive element and a second input to said comparator amplifier from said second light sensitive element and supplying an output from said comparator amplifier to said movable indicator.

* * * * *